United States Patent [19]
Makino

[11] Patent Number: 5,367,379
[45] Date of Patent: Nov. 22, 1994

[54] LUSTER DETECTOR
[75] Inventor: Kazuhiro Makino, Osaka, Japan
[73] Assignee: Keyence Corporation, Osaka, Japan
[21] Appl. No.: 899,285
[22] Filed: Jun. 16, 1992
[30] Foreign Application Priority Data
  Jun. 17, 1991 [JP] Japan .................. 3-144631
[51] Int. Cl.$^5$ ............................................. G01N 21/47
[52] U.S. Cl. ............................ 356/446; 356/445; 356/375; 356/376; 356/429; 250/341.1; 250/353
[58] Field of Search ............... 356/445, 446, 375, 376, 356/429; 250/353, 341
[56] References Cited
U.S. PATENT DOCUMENTS 4,553,033  11/1985  Hubble, III et al. ............ 250/353
4,846,578   7/1989  Morita et al. .................... 356/446

Primary Examiner—Vincent P. McGraw
Assistant Examiner—LaCharles P. Keesee, II
Attorney, Agent, or Firm—Sughrue, Mion, Zinn, Macpeak & Seas

[57] ABSTRACT

A luster detector arranged such that an output light beam of an LED is applied to a surface through a light projecting lens as an irradiating light beam having a predetermined width. Rays of light reflected from the surface are applied through a condenser lens to a line sensor. Of the rays of light reflected from the surface, the rays of light reflected regularly form a light spot on a light detecting section extending in the longitudinal direction of the light detecting section. Hence, even if the light receiving position is shifted, the light detecting operation is positively achieved. A detecting circuit determines the light reception distribution of the sensor to detect the luster of the surface.

10 Claims, 7 Drawing Sheets

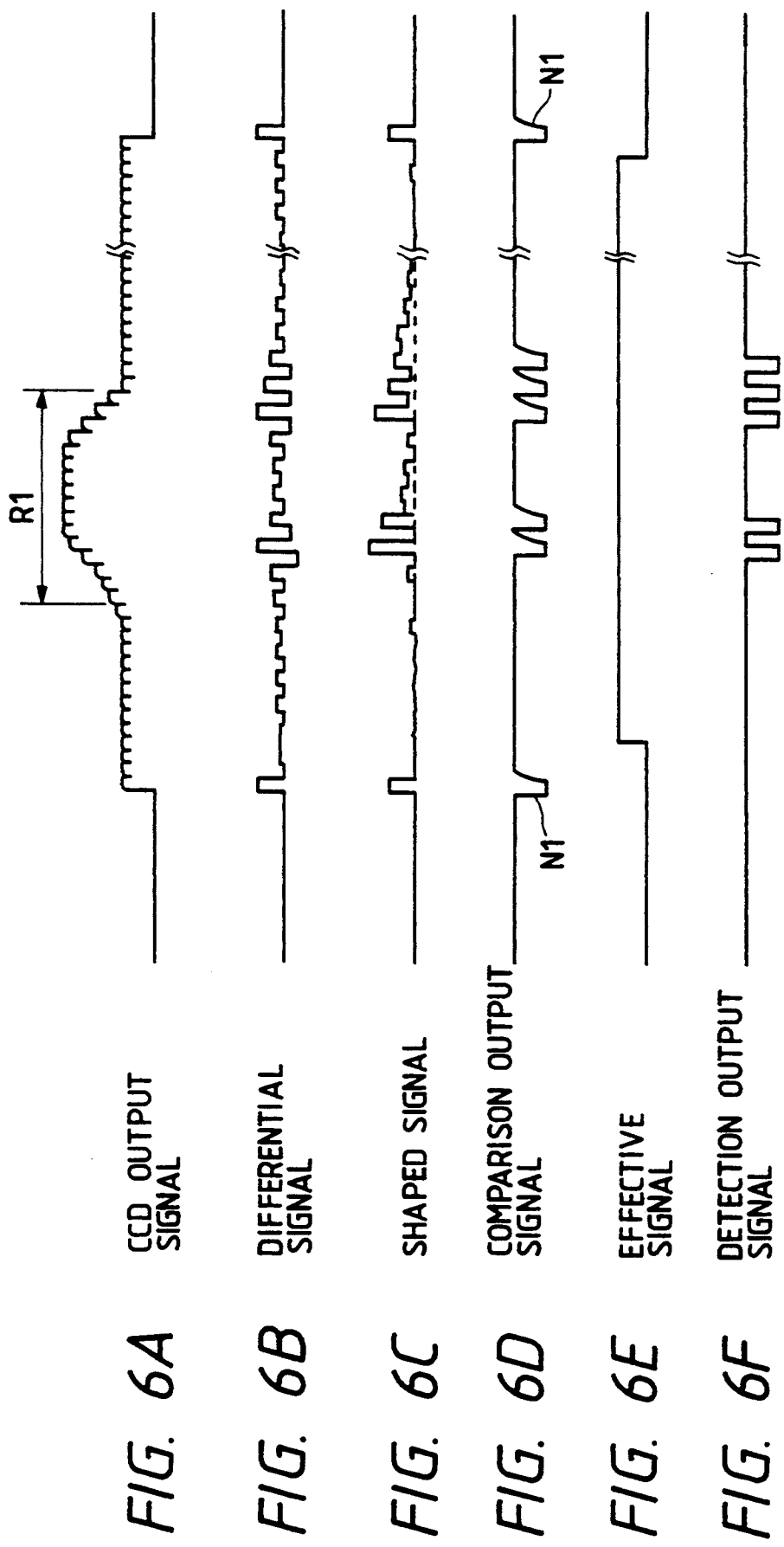

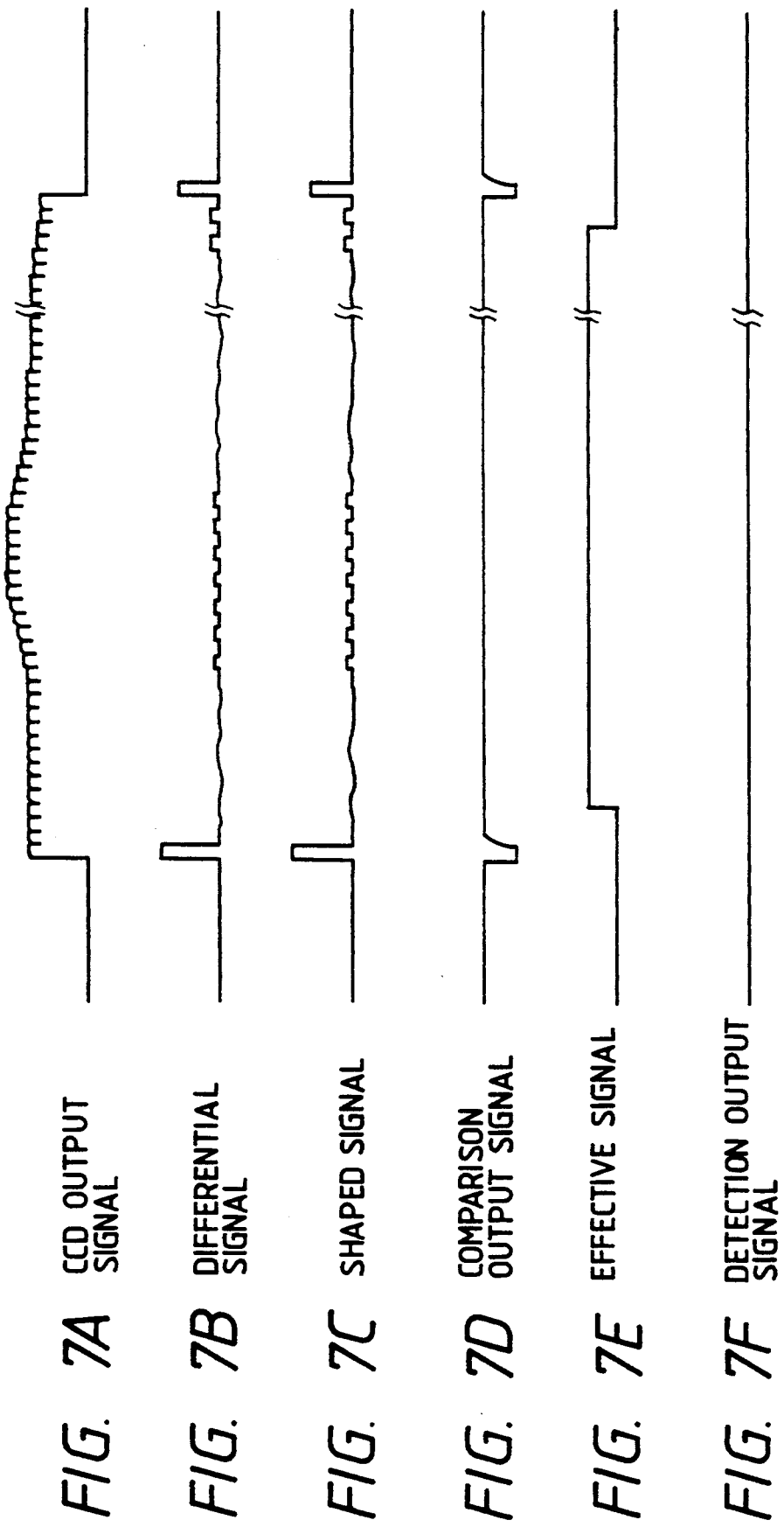

LUSTER DETECTOR

BACKGROUND OF THE INVENTION

This invention relates to a luster detector for determining whether or not a surface of an object under test is glossy.

A photo-electric switch is an example of a detector which receives light reflected from an object under test to perform a predetermined detecting operation. FIG. 8 shows a luster detector which utilizes such a photo-electric switch to detect the luster of a surface of an object under test. The luster detector includes a light emitting section 40, a regular reflection light detecting section 42, and an irregular reflection light detecting section 44. The light emitting section 40 and the regular reflection light detecting section 42 are so positioned that the angles R1 and R2 formed by light paths L1, L2 and the normal 49 of a surface M1 are equal to each other. The irregular reflection light detecting section 44 is positioned outside the light path L2 of a ray of light reflected regularly from the surface. That is, the ray of light reflected regularly from the surface under test is applied to the regular reflection light detecting section 42, and some of the rays of light diffuse-reflected therefrom are applied to the irregular reflection light detecting section 44.

The quantities of light received by the light detecting sections 42 and 44 are applied to respective circuits to provide light detection signals. The light detection signals are applied, for instance, to a substraction circuit, so that the difference between the regularly reflected light and the diffuse-reflected light is obtained, thereby to determine the glossiness of the surface M1.

When the surface M1 is high in glossiness, the quantity of light reflected regularly therefrom and applied to the regular reflection light detecting section 42 is considerably large, and therefore the quantity of light received by the regular reflection light detecting section 42 differs greatly from the quantity of light received by the irregular reflection light detecting section 44. In the case where the surface M1 is not glossy, the quantity of light diffuse-reflected therefrom is larger, and therefore the difference between the quantities of light received by the regular reflection light detecting section 42 and the irregular reflection light detecting section 44 is small. Hence, when the difference between the quantity of light reflected regularly therefrom and the quantity of light reflected irregularly therefrom is detected using the light detection signals, it can be determined whether or not the surface M1 is glossy.

However, the above-described conventional luster detector is disadvantageous for the following reason: when a number of objects are tested one after another, sometimes their surfaces M1 are inclined or shifted. If the surface is inclined as indicated at M2 in FIG. 8, then the light path of the ray of light reflected regularly therefrom is changed to a light path L7, and if the detecting surface is shifted as indicated at M3, then the light path is changed to a light path L8. In both cases, the ray of light reflected regularly from the surface is not applied to the regular reflection light detecting section 42, and accordingly it is impossible to correctly detect both the quantity of regularly reflected light and the quantity of diffuse-reflected light; that is, it is impossible to perform the luster detection operation with high accuracy. In addition, the conventional luster detector cannot handle objects of different color because the quantity of light reflected from an object's surface under test depends on the color of the latter.

SUMMARY OF THE INVENTION

Accordingly, an object of this invention is to eliminate the above-described difficulties accompanying a conventional luster detector.

More specifically, an object of the invention is to provide a luster detector in which a luster detecting operation is achieved with high accuracy even when an object's surface under test is inclined or shifted, and the effect of the color of an object's surface under test is reduced.

The foregoing object of the invention has been achieved by the provision of a luster detector which, according to the invention, comprises a light emitting section for applying light to an object's surface under test; a light detecting section including a plurality of light detecting elements which are arranged in the form of a line or plane and which produce output light detection signals according to respective quantities of light received thereby; an optical system provided for the light detecting section, the optical system gathering light reflected from the object's surface under test to form a light spot on the light detecting section using light reflected regularly from the object's surface; and luster determining means for receiving the light detection signals from the light detecting section to determine the luster of the object's surface according to the light reception distribution of the light detecting elements.

In the present luster detector, the light detecting section may comprise a line sensor having light detecting elements which are arranged linearly, and an optical system may be employed which forms a substantially elliptic or linear light spot on the light detecting section in such a manner that the light spot is extended in a direction perpendicular to the direction of arrangement of the light detecting elements in the lines sensor.

In the luster detector, an optical system may be provided for the light emitting section which forms an output light beam of the light emitting section into an irradiating light beam having a predetermined width.

Furthermore, the luster detector may be designed so that the light emitting section emits pulses of light at predetermined time intervals, and the light detection signals are read out of the light detecting section only during light detection periods corresponding to the light emission periods of the light emitting section.

In the luster detector thus organized, rays of light emitted from the light emitting section and reflected from the surface of the object under test are applied through the optical system to the light detecting section. Of the rays of light thus applied, the rays of light reflected regularly from the object's surface form a light spot on some of the light detecting elements in the light detecting section. Under this condition, the luster determining means reads the light reception distribution of the light detecting elements to determined whether or not the surface of the object under test is glossy.

In the case where the light detecting section employs a line sensor made up of light detecting elements arranged linearly, an optical system is employed for the light detecting section which forms a substantially elliptic or linear light spot which extends across the direction of arrangement of the light detecting elements. In this case, the distribution of the quantities of light received by the light detecting elements is also read to detect whether or not the surface of the object under test is glossy.

Furthermore, in the luster detector, the light emitting section emits light at predetermined time intervals, and the light detection signals are read out of the light detecting section only during light reception periods corresponding to the light emission periods of the light emitting section, which greatly reduces the effect of stray light.

BRIEF DESCRIPTION OF THE DRAWINGS

FIG. 1A is a side view, with parts cut away, showing a sensor head in the luster detector, and FIG. 1B is a plan view showing the light detecting surface of a line sensor.

FIG. 2A is a plan view showing positional relationships between the light detecting surface of the line sensor and the condenser lens, FIG. 2B is a side view of the line sensor and the condenser lens, and FIG. 2C is a front view of the line sensor and the condenser lens as viewed in the direction of the arrow 95 shown in FIG. 2B.

FIGS. 6 (A–7) are waveform diagrams showing the output signals of various circuits in FIG. 4 in the case where the surface of the object under test is high in glossiness.

FIG. 7 is a waveform diagram showing the output signals of the various circuits in FIG. 4 in the case where the surface of the object under test is low in glossiness.

DETAILED DESCRIPTION OF THE PREFERRED EMBODIMENTS

Preferred embodiments of this invention will be described with reference to the accompanying drawings.

Figure 1A:
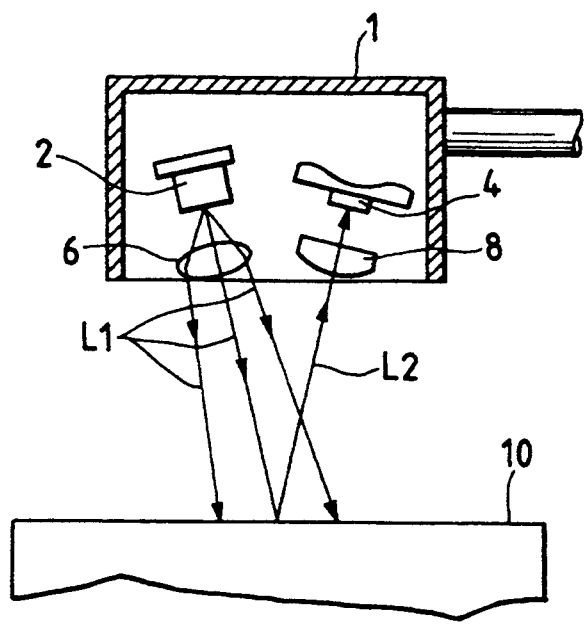
FIGS. 1A and 1B are diagrams showing one example of a luster detector according to this invention. More specifically.

FIG. 1A is a side view of a first embodiment of the invention, with parts cut away, showing a sensor head 1. The sensor head 1 incorporates a light emitting section, namely, an LED (light emitting diode) 2, and an optical system, namely, a light projecting lens 6 for the light emitting section. Light emitted from LED 2 is applied through the light projecting lens 6 to a surface 10.

A ray of light L2 reflected from the surface 10 is applied to a line sensor 4 though a condenser lens 8, which is an optical system for a light detecting section. Irradiating rays of light L1 from the LED, being diffused by the light projecting lens 6, irradiate surface 10 over a wide area. Therefore, even when surface 10 is inclined for instance, at least one light ray L2 of the rays of light reflected from surface 10 will be applied to the line sensor 4; that is, a light detecting operation is positively carried out.

Figure 1B:
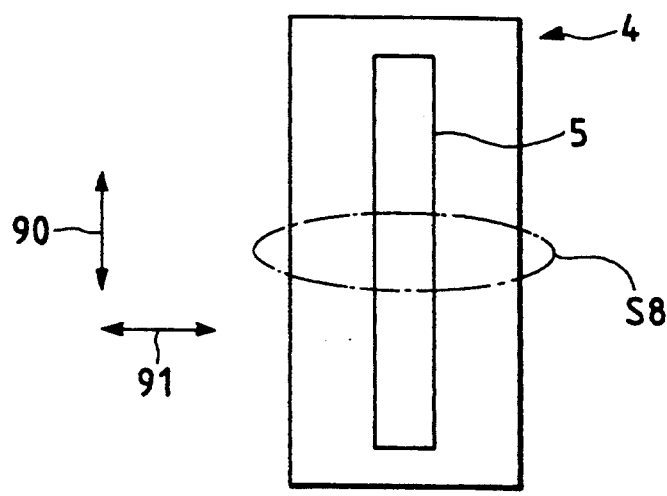

FIG. 1B is a plan view showing the light detecting surface of the line sensor 4. In this embodiment, the line sensor 4 has a light detecting section 5 made up of light detecting elements arranged linearly, and therefore it may be a one-dimensional image sensor made up of a CCD or the like. As was described above, the rays of light reflected from the surface are applied through the condenser lens 8 to the light detecting section 5. Of the rays of light thus applied, the rays of light reflected regularly from surface 10 form a substantially elliptic light spot $8 on the line sensor 4 as shown in FIG. 1B.

That is, the condenser lens 8 is so positioned that the light reflected regularly from the reflecting surface is focused on the line sensor 4. The substantially elliptic light spot S8 is elongated in a direction substantially perpendicular to the longitudinal direction of the light detecting section 5. More specifically, the light spot S8 extends across the light detecting section 5.

The light spot S8 is formed in the above-described manner. Hence, even if surface 10 is shifted or inclined so that the light spot S8 is shifted in the directions of arrow 91, the light L2 reflected regularly therefrom is applied to the light detecting section 5 without fail. Even if shifted in the directions of arrow 90, the light L2 is positively received by the light detecting section 5 because the latter 5 is made up of a plurality of light detecting elements arranged in a line, as described above.

Figure 2A:
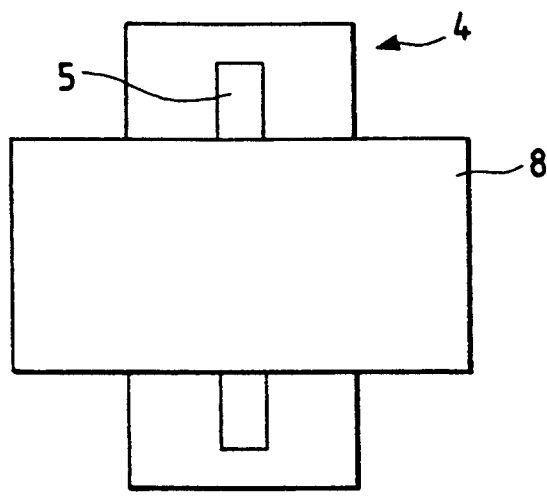
FIGS. 2A, 2B and 2C are diagrams providing a detailed description of a condenser lens shown in FIG. 1. More specifically.
Figure 2B:
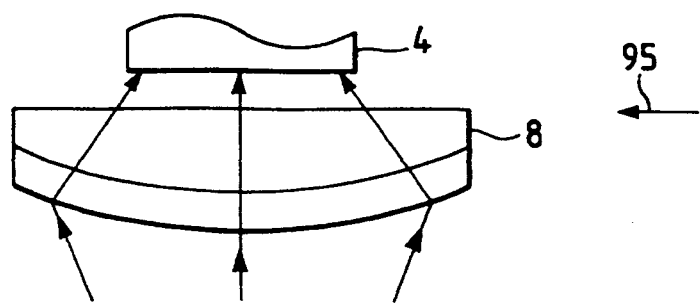

The condenser lens 8 will now be described in detail with reference to FIGS. 2A–2C. FIG. 2A shows positional relationships between the condenser lens 8 and the light detecting surface of the line sensor 4. FIG. 2B is a side view of line sensor 4 and condenser lens 8, and FIG. 2C is a front view of line sensor 4 and condenser lens 8 as viewed in the direction of arrow 95 in FIG. 2B.

Figure 2C:
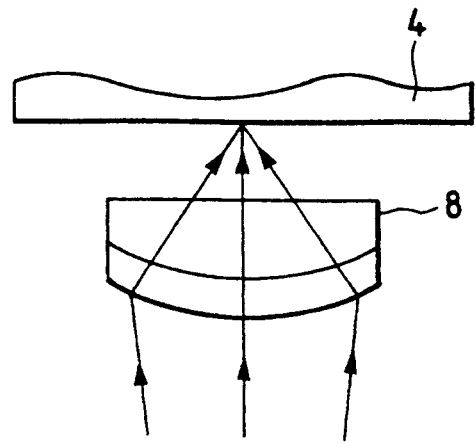

As is apparent from FIGS. 2A–2C, the condenser lens 8 is so designed that its curvature in a horizontal direction is different from that in a vertical direction. Because of this feature, its focal length in a horizontal direction is different from that in a vertical direction. When the line sensor 4 and the condenser lens 8 are so positioned that light is focused with respect to the longitudinal direction of the light detecting section 5, then a light spot S8 is formed which extends in a direction perpendicular to the longitudinal direction of the line sensor 4 and has a predetermined length. However, the optical system for the light detecting section is not limited to a lens such as the above-described condenser lens 8; that is, other optical arrangements may be employed to obtain the light spot S8.

Figure 3:
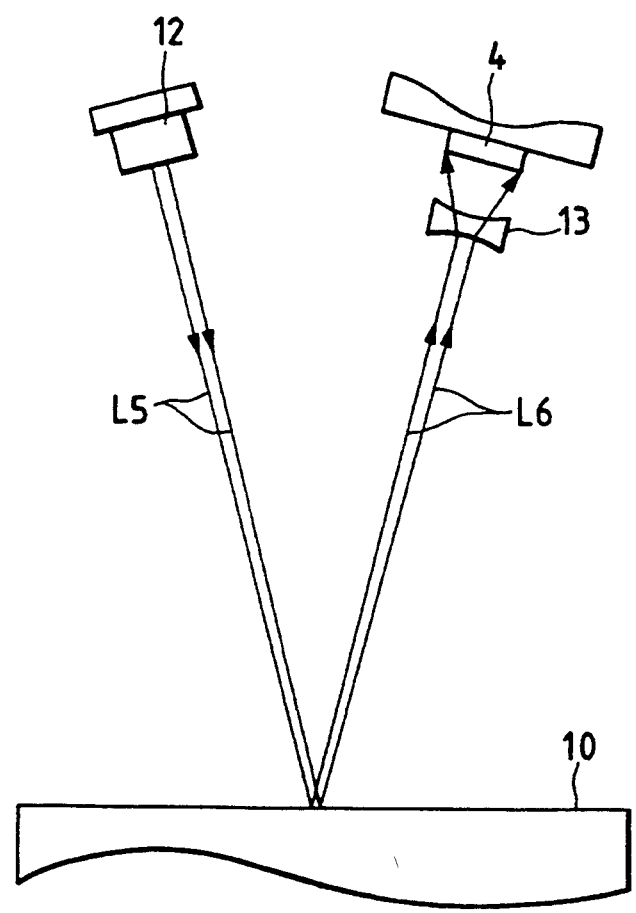
FIG. 3 is a side view showing another example of the luster detector according to the invention in which a laser beam is used to irradiate an object under test.
Figure 8:
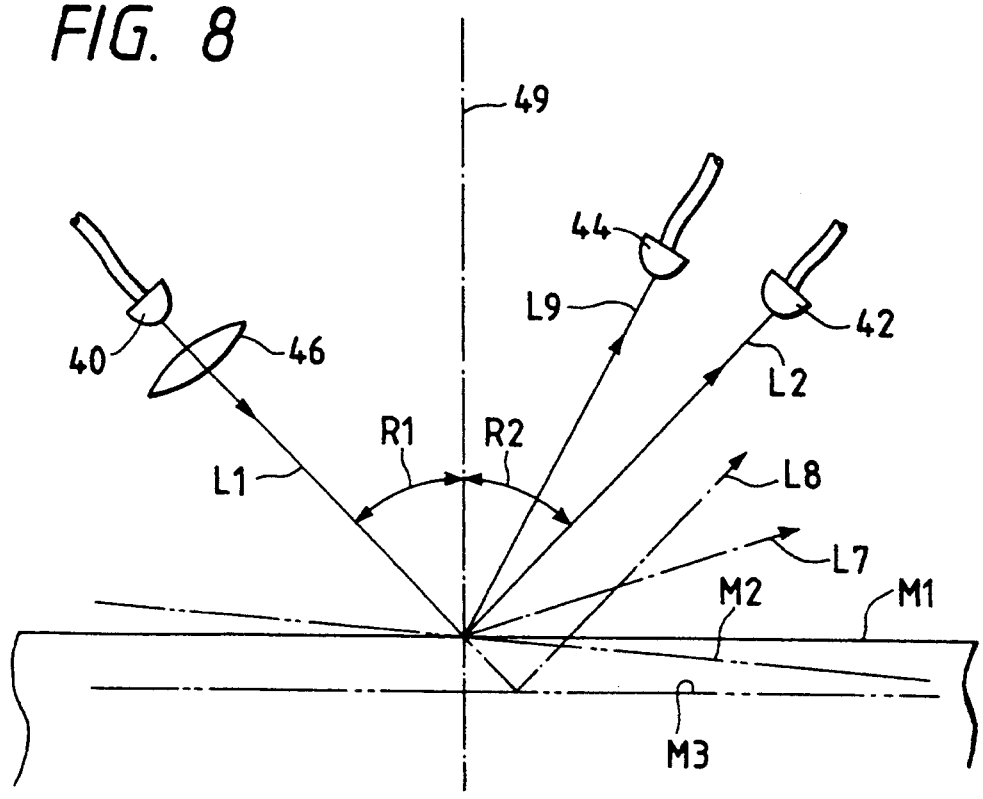
FIG. 8 is an explanatory diagram for a description of the detection mechanism of a conventional luster detector.

In the case where the luster detecting area of surface 10 is small, as shown in FIG. 3 a laser beam L5 outputted by a laser beam source 12 may be employed to irradiate the surface. In this case, the laser beam can be applied to the small area only. In irradiating the surface with the laser beam, the light beam can be concentrated, and thus the surface can be irradiated with high efficiency. In the case where the line sensor is employed, in order to form a substantially elliptic or linear light spot which extends in a direction perpendicular to the longitudinal direction of the line sensor, it is preferable to provide a concave lens 13 having a curvature in a horizontal direction different from that in a vertical direction.

In FIG. 1B, of the rays of light reflected from the surface, the rays of light reflected regularly from the latter form the light spot S8. On the other hand, the rays of light diffuse-reflected from surface 10 are also applied through the condenser lens 8 to the line sensor 4 and received by almost all of the light detecting elements (not shown). If the surface 10 is high in glossiness, then light is scarcely diffuse-reflected, and accordingly the quantity of light reflected regularly therefrom is larger; that is, of the total quantity of light received by the light detecting section 5, the quantity of light reflected regularly from the surface is much larger. In the case where the surface 10 is low in glossiness, most of the light beams applied to the surface are diffuse-reflected, so that the quantity of light reflected regularly from the surface is smaller. That is, the quantity of light received by the light detecting section is averaged as a whole.

Thus, the glossiness of the surface 10 can be determined by detecting the distribution in the quantity of light of the rays of light which are reflected from the surface and applied to the line sensor 4.

Figure 4:
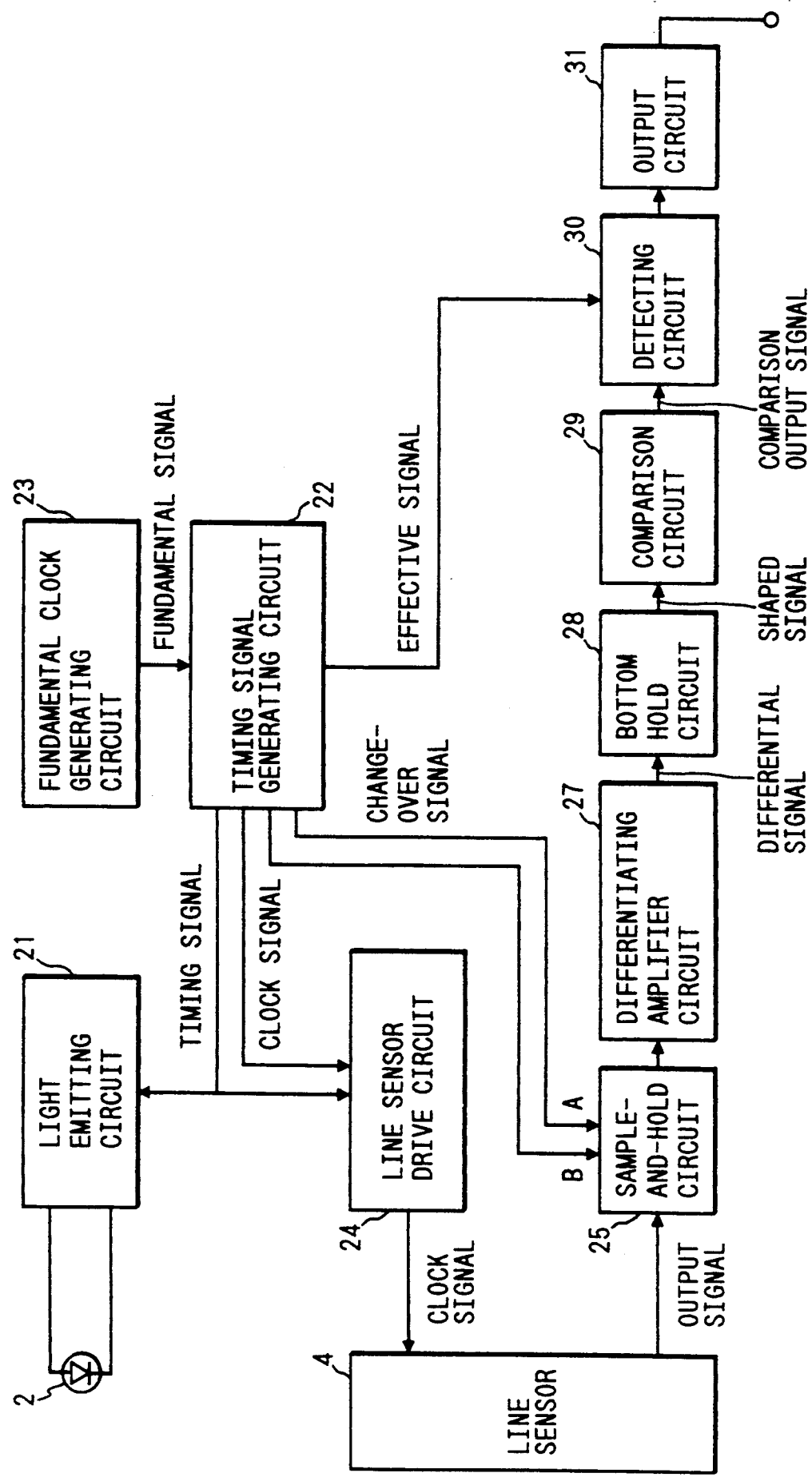
FIG. 4 is a block diagram showing one example of a detecting circuit in the luster detector according to the invention.

FIG. 4 shows one example of a detecting circuit which detects the distribution in the quantity-of light of the rays of light reflected from the surface, and controls the operation of LED 2.

A light emitting circuit 21 controls the application of the output light of the LED 2 in accordance with a timing signal provided by a timing signal generating circuit 22. The timing signal generating circuit 22 outputs signals on the basis of a fundamental signal provided by a fundamental clock generating circuit 23, and applies the timing signal to both the light emitting circuit 21 and a line sensor drive circuit 24.

In response to the timing signal, the line sensor drive circuit 24 controls the light detecting period of the line sensor 4. The line sensor drive circuit 24 utilizes a so-called "shutter function" provided originally for the line sensor 4 to allow the latter to perform a light detecting operation only during light emission period (i.e., only when LED 2 emits light). This effectively eliminates the difficulty of stray light being received during periods other than the light emission period. Hence, the detecting operation is achieved with high accuracy.

The line sensor 4, receiving light reflected from the surface 10, applies the light detection signals of the light detecting elements to a sample-and-hold circuit 25. More specifically, the line sensor 4 applies the light detection signals to the sample-and-hold circuit in response to the clock signal which is applied thereto through the line sensor drive circuit 24 by the timing signal generating circuit 22; that is, the light detection signals are applied to the sample-and-hold circuit 25 successively beginning with the light detection signal of the first of the light detecting elements. The waveform of the output of the line sensor 4 is shown in FIG. 6A. The output waveform is produced when a surface under test is glossy. In FIG. 6A, a waveform region R1 higher in level corresponds to the quantity of light reflected regularly from the surface.

Figure 5:
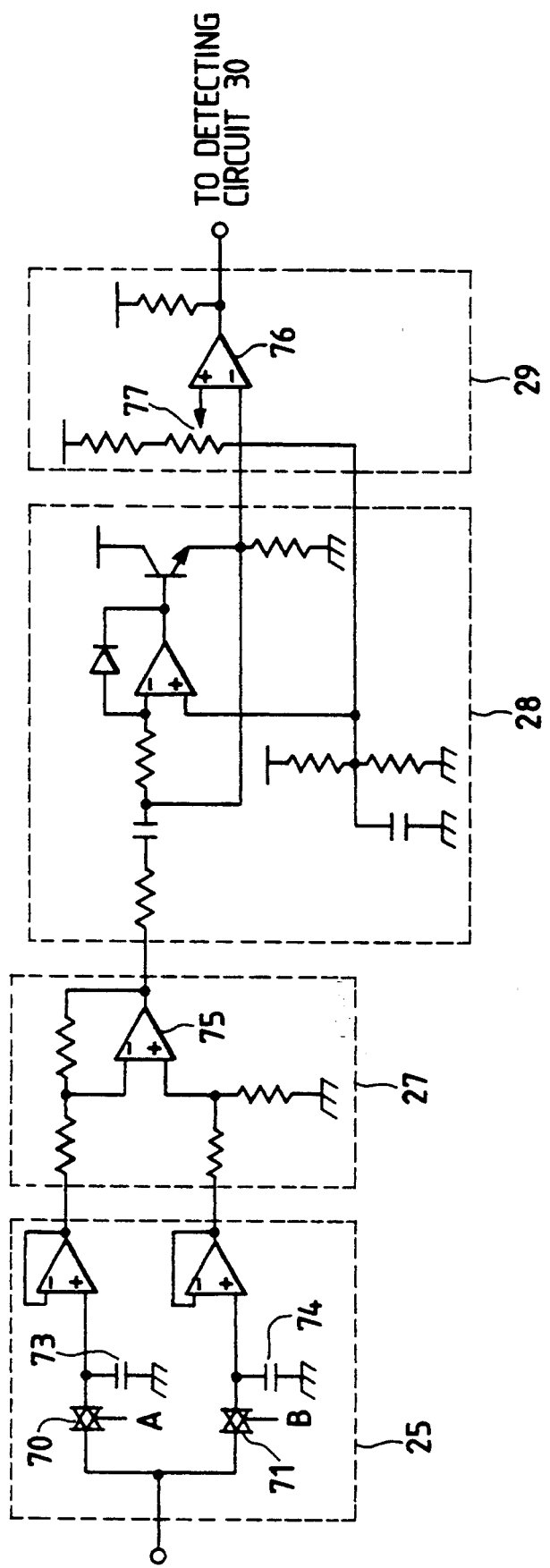
FIG. 5 is a circuit diagram showing details of a sample-and-hold circuit, a differentiating amplifier circuit, a bottom hold circuit, and a comparison circuit in FIG. 4.

The sample-and-hold circuit 25 holds the output signals of the light detecting elements, and applies them to a differentiating amplifier circuit 27. In the differentiating amplifier circuit 27, the amounts of variation of those output signals are obtained to determine whether or not the detected surface is glossy. FIG. 5 shows the sample-and-hold circuit 25, the differentiating amplifier circuit 27, a bottom hold circuit 28, and a comparison circuit 29 in detail.

The sample-and-hold circuit 25 has analog switches 70 and 71, to which change-over signals A and B are applied by the timing signal generating circuit 22. The analog switches 70 and 71 are so designed that, when the change-over signal A is applied to circuit 25, analog switch 70 is opened while analog switch 71 is closed, and when the change-over signal B is applied to the circuit 25, the analog switch 70 is closed while the analog switch 71 is opened.

The timing signal generating circuit 22, in response to the clock signal applied to the line sensor 4, outputs the change-over signal A when an odd-numbered light detecting element in the array of light detecting elements produces an output signal (hereinafter referred to as "an odd-numbered output signal"), and the change-over signal B is applied when an even-numbered light detecting element therein produces an output signal (hereinafter referred to as "an even-numbered output signal"). That is, the analog switches are turned on and off in response to the odd-numbered and even-numbered output signals. The odd-numbered output signal is stored in a capacitor 73, and the even-numbered output signal is stored in a capacitor 74.

The value held by the capacitor 73 is applied to the inverting (−) input terminal of an operational amplifier 75 in the differential amplifier circuit 27, and the value held by the capacitor 74 is applied to the noninverting (+) input terminal of the operational amplifier 75, so that the difference between those values is outputted as a differential signal. The waveform of the differential signal is shown in FIG. 6B. The odd-numbered and even-numbered output signals of the light detecting elements are alternately held by the sample-and-hold circuit 25, so that a differential signal as shown in FIG. 6B is obtained based on the difference between adjacent output signals.

The differential signal is applied to the bottom hold circuit 28, where the negative minimum value of the waveform of the differential signal is raised to a predetermined level to provide a shaped signal. The shaped signal provided by the bottom hold circuit 28 is shown in FIG. 6C. The provision of the shaped signal makes it possible to detect the amount of variation of the output signal more positively.

The shaped signal is applied to the inverting (−) input terminal of an operational amplifier 76 in the comparison circuit 29, where it is compared with a threshold value, set with a variable resistor 77, to provide a comparison output signal. The waveform of the comparison output signal is shown in FIG. 6D. The threshold value can be set to a desired value by operating the variable resistor 77.

In the case where an object's surface under test is high in glossiness, the rays of light reflected regularly therefrom are high in intensity, so that the output signals of the light detecting elements covered by the light spot S8 are greatly different from those of the remaining light detecting elements. More specifically, the difference between the output signals of light detecting elements located near the periphery of the light spot S8 is large, so that pulse signals appear in the comparison output signal of the comparison circuit 29 as shown in FIG. 6D.

The output of the first light detecting element changes abruptly at the rising edge, and the output of the last light detecting element also changes abruptly at the falling edge. Hence, the output of the comparison circuit 29 unavoidably includes signals N1.

However, this effect is not related to glossiness. In order to disregard signals N1, an effective signal E is produced with the timing limited within the period of the output signal of the light detecting element, and a detecting circuit 30 detects the comparison output signal D for the period of the effective signal to provide a detection output signal F.

Let us consider the light detection signals produced in response to one emission of light from the LED 2, which emits light at predetermined time intervals. If, in this case, the outputs of adjacent light detecting elements are greatly different from each other, then it may be considered that the surface under test is glossy. Hence, when the detection output signal F includes pulse signals, a signal is applied to an output circuit 31 to indicate the fact that the surface is glossy. In this connection, with disturbance light, voltage variation and other noises taken into account, the output circuit 31 outputs a luster detection signal when it has received the output signal of the detecting circuit 30 a predetermined number of times (for instance four times) continuously.

FIG. 7 shows the waveforms of the output signals provided when a surface is relatively low in glossiness. In this case, the rays of light reflected from the surface and received by the line sensor 4 are averaged, and therefore the deviation between the output signals of the light detecting elements is not great; that is, it is determined that the surface is not glossy.

As was described above, LED 2 emits pulse light. In the line sensor, the light detecting elements form charges according to the amounts of light received, to provide the output signals. If disturbance light is applied to the light detecting elements during time intervals that the LED does not emit light, then, the amount of charge received by the light detecting elements is increased, with the result that it becomes impossible to correctly detect the light beams reflected from surface 10. In order to eliminate this difficulty, the line sensor has a shutter function to discharge the light detecting elements in synchronization with the light emission period of the LED 2, thereby minimizing the effect of the disturbance light.

The light detecting section may be made up of an area sensor which is formed by arranging light detecting elements in a plane, or a two-dimensional image sensor implemented with a CCD or the like.

In the above-described embodiment, the digital differentiating circuit 27 is employed to detect the rates of change of the output signals of the light detecting elements. However, the invention is not limited thereto or thereby. That is, the detection may be carried out with an analog differentiating circuit (not shown). In addition, it should be noted that, instead of the rates of change of the output signals of the light detecting elements, the amounts of change of the maximum and minimum values thereof may be used for detection of luster.

In the luster detector of the invention, the light detecting section is made up of a plurality of light detecting elements arranged one dimensionally or two dimensionally. Therefore, it can positively receive light even when an object under test is shifted or inclined; that is, the luster of the surface can be detected with high accuracy. Furthermore, the luster determining circuit performs its operation in accordance with the light reception distribution of the light detecting elements and the ratio of the quantities of light received thereby. Therefore, the effect of the color of the object under test is reduced.

In the case where the light detecting section employs the line sensor, the resultant luster detector is simple in circuitry, high in the speed of response, and is able to perform its operation positively. Furthermore, the luster detector is low in manufacturing cost, and can be miniaturized.

The light detecting section employs the optical system which forms the substantially elliptic or linear light spot in such a manner that it extends in a direction perpendicular to the direction of arrangement of the light detecting elements in the line sensor. Therefore, the light reflected regularly from the surface can be positively focused on the line sensor and is not affected by displacement or inclination of the object under test.

Furthermore, in the luster detector of the present invention, the light detection signals of the light detecting section are read only during the light reception periods corresponding to the light emission periods, which substantially eliminates the adverse effect of disturbance light.

What is claimed is:

1. A luster detector comprising:
    a light emitting section for applying light to a surface under test;
    a light detecting section including a line sensor having a plurality of light detecting elements arranged linearly, and which output light detection signals according to respective quantities of light received thereby;
    an optical system provided for said light detecting section, said optical system gathering light reflected from said surface under test to form a light spot on said light detecting section from light reflected regularly from said surface, said light spot being formed in such a manner to define a lengthwise dimension thereof which is substantially larger than a widthwise dimension thereof and which is perpendicular to the direction of arrangement of said light detecting elements; and luster determining means receiving said light detection signals from said light detecting section to determine the luster of said surface according to a light reception distribution of said light detecting elements.

2. A luster detector as claimed in claim 1, wherein said plurality of light detecting elements are arranged in the form of a plane.

3. A luster detector as claimed in claim 1, wherein said optical system forms a substantially elliptic light spot on said light detecting section.

4. A luster detector as claimed in claim 1, wherein said optical system forms a substantially linear light spot on said light detecting section.

5. A luster detector as claimed in claim 1, further comprising:
    an optical system for said light emitting section for forming an output light beam of said light emitting section into an irradiating light beam having a predetermined width.

6. A luster detector as claimed in claim 1, wherein
    said light emitting section emits pulse light at predetermined time intervals, and
    said light detection signals are read out of said light detecting section only during light detection periods corresponding to the light emission periods of said light emitting section.

7. A method of detecting whether or not the surface of an object under test is glossy, comprising the steps of:
- irradiating the surface at predetermined time intervals;
- forming light rays regularly reflected from the surface during said predetermined time intervals into a substantially elliptic light spot onto a light detecting section, said light spot extending substantially perpendicular to a longitudinal direction of the light detecting section;
- generating light detection signals corresponding to said light rays regularly reflected form the surface;
- generating light detection signals corresponding to said light rays diffuse-reflected from the surface;
- determining a difference between said light detection signals corresponding to said light rays regularly reflected from the surface and said light detection signals corresponding to said light rays diffuse-reflected from the surface; and
- determining that the surface is glossy when the difference between said light detection signals corresponding to said light rays regularly reflected from the surface and said light detection signals corresponding to said light rays diffuse-reflected from the surface is larger than a predetermined value.

8. A method as claimed in claim 7, wherein said light rays regularly reflected from the surface form a substantially elliptic light spot on said light detecting section.

9. A method as claimed in claim 7, wherein said light rays regularly reflected from the surface form a substantially linear light spot on said light detecting section.

10. A luster detector comprising:
- a light emitting section for applying light to a surface under test;
- a light detecting section which outputs light detection signals according to the quantity of light received thereby;
- an optical system provided for said light detecting section, said optical system gathering light reflected from said surface under test to form a light spot on said light detecting section from light reflected regularly from said surface said light spot being formed in such a manner to define a lengthwise dimension thereof which is substantially larger than a widthwise dimension thereof; and
- luster determining means receiving said light detection signal from said light detecting section to determine the luster of said surface.

* * * * *